United States Patent [19]

McKinley et al.

[11] Patent Number: 4,500,670

[45] Date of Patent: Feb. 19, 1985

[54] COMPOSITE MIXTURES FOR IMPROVING GEL STRENGTH OF WATER ABSORBENT GELS

[75] Inventors: Mark J. McKinley, Linwood; Dan P. Sheridan, Saginaw, both of Mich.

[73] Assignee: The Dow Chemical Company, Midland, Mich.

[21] Appl. No.: 554,156

[22] Filed: Nov. 22, 1983

[51] Int. Cl.$^3$ .............................. C08K 3/34
[52] U.S. Cl. ........................ 524/445; 106/93; 106/97; 106/99; 523/111; 524/446; 524/447; 524/534; 524/555; 524/904; 524/916; 604/364
[58] Field of Search ............ 524/555, 534, 445, 446, 524/447; 106/93, 99, 97

[56] References Cited

U.S. PATENT DOCUMENTS

| | | | |
|---|---|---|---|
| 2,930,317 | 3/1960 | Perkins | 524/555 |
| 3,050,486 | 8/1962 | Ritson et al. | 524/555 |
| 3,057,811 | 10/1962 | Trachtenberg et al. | 428/452 |
| 3,530,080 | 9/1970 | Inskip | 428/478.8 |
| 3,900,378 | 8/1975 | Yen et al. | 204/159.14 |
| 3,909,421 | 9/1975 | Gaddis | 252/855 D |
| 3,935,363 | 1/1976 | Burkholder et al. | 428/281 |
| 4,021,257 | 5/1977 | Bernett | 106/93 |
| 4,043,827 | 8/1977 | Bernett | 106/93 |
| 4,058,124 | 11/1977 | Yen et al. | 524/445 |
| 4,076,673 | 2/1978 | Burkholder | 524/389 |
| 4,128,528 | 12/1978 | Fisque et al. | 524/447 |
| 4,209,568 | 6/1980 | Clem | 428/911 |
| 4,254,008 | 3/1981 | Krsek | 524/388 |
| 4,272,514 | 6/1981 | Spence | 524/451 |
| 4,278,583 | 7/1981 | Sekiya | 428/511 |
| 4,293,609 | 10/1981 | Erickson | 428/284 |
| 4,351,754 | 9/1982 | Dupré | 524/445 |
| 4,367,297 | 1/1983 | Hubner et al. | 524/407 |
| 4,372,311 | 2/1983 | Potts | 428/332 |
| 4,402,752 | 9/1983 | Chesney | 106/98 |
| 4,405,744 | 9/1983 | Greinecker et al. | 524/445 |
| 4,411,800 | 10/1983 | Green et al. | 252/8.5 A |
| 4,412,018 | 10/1983 | Finlayson et al. | 524/445 |
| 4,418,163 | 11/1983 | Murakami et al. | 524/445 |
| 4,424,247 | 1/1984 | Erickson | 428/284 |

*Primary Examiner*—Herbert J. Lilling

[57] ABSTRACT

Water absorbent compositions exhibiting increased gel strengths comprise a water-swellable hydrophilic polymer and an inorganic powder and are prepared by physically blending the polymer and powder. The compositions can be incorporated into film laminates and can be employed in preparing improved disposable diapers.

22 Claims, No Drawings

COMPOSITE MIXTURES FOR IMPROVING GEL STRENGTH OF WATER ABSORBENT GELS

BACKGROUND OF THE INVENTION

The present invention relates to polymeric agents which are useful as water absorbents, and in particular, to polymeric agents which are useful in removing water from numerous systems.

Water-swellable polymers have found various uses as absorbents for water. Examples of such polymers are disclosed in U.S. Pat. Nos. 3,926,891; 4,190,562 and 4,293,609. Unfortunately, such known water-swellable polymers have limited gel strength. The low gel strengths of such polymers introduce integrity problems to water absorbent systems resulting in poor handling problems as well as poor product efficiency (i.e. poor utilization of water absorbent capacity). Thus, although water absorbent polymers have high water absorbent capabilities, the utilization of such polymers has been severely limited. Gel strengths can be increased by increasing the amount of crosslinking agent in the polymer. However, such polymers are very rigid gels which are difficult to produce and difficult to handle.

In view of the deficiencies of the prior art, it would be highly desirable to provide a water absorbent composition having high water absorbent capacity and increased gel strength.

SUMMARY OF THE INVENTION

The present invention is an improved water absorbent composition comprising (1) a water absorbing amount of a water-swellable hydrophilic polymer and (2) an inorganic powder (i.e., filler) in an amount sufficient to increase gel strength exhibited by said water absorbent composition, wherein said composition is prepared by physically blending said inorganic powder with said polymer, and wherein said polymer is blended with said powder after the polymer has been polymerized.

In another aspect, the present invention is a method for increasing the gel strength of a water absorbent composition comprising a water absorbent amount of a water-swellable hydrophilic polymer wherein an inorganic powder is blended with said polymer in an amount sufficient to increase the gel strength of said water absorbent composition, said method comprising the physical blending of said inorganic powder with said polymer, and wherein said polymer is blended after it has been polymerized.

The composition of this invention provides the skilled artisan with the means for effectively absorbing water in the form of an aqueous medium or moisture wherein the increased gel strength of the water absorbent composition is desirable. The composition of this invention can be employed in a wide variety of applications in which water and moisture absorbent materials have been employed.

DETAILED DESCRIPTION

The water-swellable hydrophilic polymers useful in this invention can be any of the known hydrophilic polymers that can be constructed in a composite of polymeric absorbent and inorganic filler. Preferred hydrophilic polymers are lightly crosslinked. Such hydrophilic polymers include acrylic copolymers, starch/graft copolymers, water-insoluble alkali salt of saponified, gelatinized starch/polyacrylonitrile graft polymers, and the like. Examples of suitable polymers are disclosed in U.S. Pat. Nos. 3,997,484; 3,926,891; 3,395,099; 4,090,013; 4,190,562; 4,405,387. Especially preferred polymers are disclosed in U.S. Pat. Nos. 4,117,184; 4,176,677; 4,293,609; and U.S. Patent Office application Ser. No. 319,538, filed Nov. 9, 1981, now U.S. Pat No. 4,424,247; which are incorporated herein by reference.

The preferred hydrophilic polymers useful in this invention are polyelectrolytes exemplary of which are ammonium or alkali metal salts of homopolymers of acrylic or methacrylic acid, and copolymers thereof with one or more ethylenically unsaturated comonomers. Examples of suitable monomers useful in preparing polymers; polymers and copolymers; crosslinking agents; etc. are disclosed in the aforementioned U.S. patent application Ser. No. 319,538.

Also useful of this invention are polymers comprising polymerized sulfonate monomers which can be used in place of or in addition to the acrylate monomers. Examples of suitable water-soluble, ethylenically unsaturated sulfonate monomers include N-sulfoalkyl, $\alpha,\beta$-ethylenically unsaturated amide salts such as the alkali metal salts of 2-acrylamido-2-methylpropane sulfonic acid, 2-acrylamido propane sulfonic acid, 2-acrylamido ethane sulfonic acid as well as other such monomers listed in U.S. Pat. No. 3,692,673 which is hereby incorporated by reference alkali metal salts of sulfoalkyl esters of unsaturated carboxylic acids such as 2-sulfoethyl methacrylate and other such sulfoalkyl esters as listed in U.S. Pat. No. 4,075,134 which is also incorporated by reference; salts of sulfoarylalkenes such as vinylbenzyl sulfonic acid and the various salts of vinylbenzyl sulfonate, p-styrene sulfonic acid, salts of sulfoalkenes such as vinyl sulfonic acid, and the like. Of the foregoing sulfonate monomers, the sulfoalkyl derivatives of acrylamide and methacrylamide are preferred with those of acrylamide being especially preferred, particularly the sodium and potassium salts of 2-acrylamido-2-methylpropane sulfonic acid (AMPS), and 2-acrylamido-2-propane sulfonic acid. In the most preferred embodiments, the sulfo group is in the form of an alkali metal sulfonate such as sodium sulfonate.

For the purpose of this invention, a moisture absorbent or water-swellable polyelectrolyte or polymer is one that absorbs several times its weight of an aqueous liquid, preferably more than about 15 times its weight in water. The amount of water which a particular polymer will absorb (i.e., the water absorbent capacity) is dependent upon the pH of the aqueous medium which is being absorbed, the molecular weight of the polymer, the amount of ionic character of the polymer, and the amount of crosslinking in the polymer.

By the term "powder" is meant a very finely divided water insoluble or sparingly water-soluble grouping or agregate of solid particles, usually smaller than 1,000 $\mu$m. Inorganic powders especially preferred herein include a wide variety of clays. Specific examples include sodium bentonite (montmorillonite clay), kaolinite and attapulgite. Other inorganic powders include, for example, white carbon, synthetic silicate, white carbon, basic magnesium carbonate, ultrafine magnesium silicate, light or heavy calcium carbonate, soft or hard clays, talc, vermiculite, pearlite, barium sulfate, mica, and the like.

The compositions of this invention are prepared by blending the desired polymer with the desired inorganic powder. Although the materials can be physically blended using a wide variety of means, dry blending is preferred. That is, essentially dry polymer is physically mixed with the desired essentially dry inorganic powder. Thorough mixing insures good gel strength of the composition. Generally the order of addition of components is not particularly critical.

The amount of polymer employed in this invention can range from about 1 to about 99, preferably from about 20 to about 90, most preferably from about 40 to about 75, especially preferably from about 50 to about 60, weight percent of polymer based on the total weight of the polymer and filler. Conversely, the amount of inorganic powder useful herein ranges from about 1 to about 99, preferably from about 10 to about 80, most preferably from about 25 to about 60, especially preferably from about 40 to about 50, weight percent of said inorganic powder based on the total weight of the polymer and filler.

The compositions of this invention exhibit increased gel strengths over those compositions containing a polymer and not containing the inorganic powder. The high gel strengths of such compositions allow for products exhibiting good utilization of water absorbent capacity as well as good integrity. In this regard, the compositions of this invention are easy to handle and can be employed in a wider variety of applications as have water absorbent materials been previously employed.

The compositions of this invention can be incorporated into film laminates and other such materials as are described, for example, in U.S. Pat. Nos. 4,117,184; 4,176,677; 4,293,609 and the aforementioned U.S. Pat. Office application Ser. No. 319,538. For example, thoroughly mixed powder/polymer compositions can be incorporated in wicking substrates and treated as described in U.S. Pat. No. 4,293,609. Such materials exhibit high water absorbent capabilities, good integrity and resistance to separation of polymer and inorganic powder.

Uses of the increased gel strength composition of the present invention include applications such as shut-off filters for fuels such as gasoline, oil, hydraulic fluids, and the like. Other applications include the incorporation of such compositions, as is necessary, in disposable diapers, and other personal hygiene products and applications.

The following examples are presented to further illustrate but not limit the scope of this invention.

EXAMPLE 1

A crosslinked polyacrylamide polymer having a molecular weight of about 4 million which is crosslinked with about 500 ppm methylene bisacrylamide is dry blended with sodium bentonite in a Waring Blendor. The weight ratio of polymer to clay is about 50/50. About 1 gram (g) of this composite is dispersed in 50 g of deionized water. After 20 minutes the composite gel/water mixture is filtered through a 115 mesh nylon screen. The gel is allowed to drip dry on the screen for 20 minutes. The gel is scraped from the wire mesh with a spatula and placed onto a 1.5 inch diameter cylinder which is equiped with a 20 mesh wire screen at the bottom end. Enough of the gelled composition is added to provide a 1 inch height of gel in the 1.5 inch diameter cylinder. A spatula is then used to make a small hole in the gel that runs from the top of the gel to the bottom of the screen in order to allow trapped air to escape. A weighed piston is then placed onto the cylinder which presses the gel onto the screen. An empty quart jar is placed on top of the piston and enough water is added until a small quantity of gel is extruded through the wire screen. The weight of the jar plus water and that of the piston is used in order to determine the gel strength. Data concerning the gel strength of the composition is presented in Table I.

TABLE I

| Sample No. | Percent Inorganic Powder | Percent Water-Swellable Polymer | Gel[1] Strength (p.s.i) |
|---|---|---|---|
| 1 | 90 | 10 | <0.1 |
| 2 | 75 | 25 | 0.9 |
| 3 | 50 | 50 | 1.6 |
| 4 | 40 | 60 | 2.1 |
| 5 | 25 | 75 | 1.5 |
| 6 | 10 | 90 | 0.4 |
| C-1* | 0 | 100 | <0.1 |

*Not an example of the invention.
[1]The gel strength in pounds per square inch (p.s.i.) is determined by dividing the total weight on the gel by the area of the piston.

The data in Table I indicates that good gel strengths are observed for those compositions containing a blend of inorganic and water-swellable polymer.

What is claimed is:

1. An improved water absorbent composition comprising (1) a water absorbing amount of a lightly crosslinked, water-swellable hydrophilic polymer and (2) an inorganic powder in an amount sufficient to increase gel strength exhibited by said water absorbent composition, wherein said composition is prepared by physically blending said inorganic powder with said polymer and wherein said powder is blended with said polymer after the polymer has been polymerized and crosslinked.

2. A method for increasing the gel strength of a water absorbent composition comprising a water absorbent amount of a crosslinked water-swellable hydrophilic polymer wherein an inorganic powder is blended with said polymer in an amount sufficient to increase the gel strength of said water absorbent composition, said method comprising the physical blending of said inorganic powder with said polymer, and wherein said powder is blended with said polymer after the polymer has been polymerized and crosslinked.

3. A composition of claim 1 wherein said inorganic powder is a clay.

4. A method of claim 2 wherein said inorganic powder is a clay.

5. A composition of claim 1 wherein the amount of said polymer ranges from about 1 to about 99 weight percent, and the amount of said inorganic powder ranges from about 1 to about 99 weight percent, based on the total weight of the polymer and inorganic powder.

6. A method of claim 2 wherein the amount of said polymer ranges from about 1 to about 99 weight percent, and the amount of said inorganic powder ranges from about 1 to about 99 weight percent, based on the total weight of the polymer and inorganic powder.

7. A composition of claim 1 wherein the amount of said polymer ranges from about 20 to about 90 weight percent, and the amount of said inorganic powder ranges from about 10 to about 80 weight percent, based on the total weight of the polymer and inorganic powder.

8. A method of claim 2 wherein the amount of said polymer ranges from about 20 to about 90 weight percent, and the amount of said inorganic powder ranges from about 10 to about 80 weight percent, based on the total weight of the polymer and inorganic powder.

9. A composition of claim 1 wherein the amount of said polymer ranges from about 40 to about 75 weight percent, and the amount of said inorganic powder ranges from about 25 to about 60 weight percent, based on the total weight of the polymer and inorganic powder.

10. A method of claim 2 wherein the amount of said polymer ranges from about 40 to about 75 weight percent, and the amount of said inorganic powder ranges from about 25 to about 60 weight percent, based on the total weight of the polymer and inorganic powder.

11. A composition of claim 1 wherein the amount of said polymer ranges from about 50 to about 60 weight percent, and the amount of said inorganic powder ranges from about 40 to about 50 weight percent, based on the total weight of the polymer and inorganic powder.

12. A method of claim 2 wherein the amount of said polymer ranges from about 50 to about 60 weight percent, and the amount of said inorganic powder ranges from about 40 to about 50 weight percent, based on the total weight of the polymer and inorganic powder.

13. A composition of claim 1 wherein essentially dry polymer is physically blended with essentially dry inorganic powder.

14. A method of claim 2 wherein essentially dry polymer is physically blended with essentially dry inorganic powder.

15. A composition of claim 3 wherein said clay is sodium bentonite or attapulgite.

16. A method of claim 4 wherein said clay is sodium bentonite or attapulgite.

17. A composition of claim 1 wherein said powder is a grouping or aggregate of solid particles smaller than 1000 $\mu$m.

18. A method of claim 2 wherein said powder is a grouping or aggregate of solid particles smaller than 1000 $\mu$m.

19. A composition of claim 1 wherein said water-swellable hydrophilic polymer contains polymerized monomers of N-sulfoalkyl, $\alpha,\beta$-ethylenically unsaturated salts.

20. A method of claim 2 wherein said water-swellable hydrophilic polymer contains polymerized monomers of N-sulfoalkyl, $\alpha,\beta$-ethylenically unsaturated salts.

21. A composition of claim 1 wherein said powder is a synthetic silicate.

22. A method of claim 2 wherein said powder is a synthetic silicate.

* * * * *

REEXAMINATION CERTIFICATE (2444th)
United States Patent [19]
McKinley et al.

[11] B1 4,500,670

[45] Certificate Issued Dec. 27, 1994

[54] COMPOSITE MIXTURES FOR IMPROVING GEL STRENGTH OF WATER ABSORBENT GELS

[75] Inventors: Mark J. McKinley, Linwood; Dan P. Sheridan, Saginaw, both of Mich.

[73] Assignee: The Dow Chemical Company, Midland, Mich.

Reexamination Request:
No. 90/003,057, May 17, 1993

Reexamination Certificate for:
Patent No.: 4,500,670
Issued: Feb. 19, 1985
Appl. No.: 554,156
Filed: Nov. 22, 1983

[51] Int. Cl.⁵ ............................................. C08K 3/34

[52] U.S. Cl. ............................ 524/445; 523/111; 524/446; 524/447; 524/534; 524/555; 524/904; 524/916; 524/5; 604/364

[58] Field of Search ............... 524/445, 446, 447, 534, 524/555, 904, 916; 523/111

[56] References Cited

U.S. PATENT DOCUMENTS

| | | | |
|---|---|---|---|
| 4,179,367 | 12/1979 | Barthell et al. | 210/41 |
| 4,272,514 | 6/1981 | Spence | 424/69 |
| 4,286,082 | 8/1981 | Tsubakimoto et al. | 526/240 |
| 4,351,754 | 9/1982 | Dupré | 524/445 |
| 4,418,163 | 11/1983 | Murakami et al. | 523/205 |

*Primary Examiner*—Paul R. Michl

[57] ABSTRACT

Water absorbent compositions exhibiting increased gel strengths comprise a water-swellable hydrophilic polymer and an inorganic powder and are prepared by physically blending the polymer and powder. The compositions can be incorporated into film laminates and can be employed in preparing improved disposable diapers.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-22 having been finally determined to be unpatentable, are cancelled.

* * * * *